United States Patent [19]

King et al.

[11] Patent Number: 5,552,398
[45] Date of Patent: Sep. 3, 1996

[54] AZABICYCLIC COMPOUNDS AS 5-HT4 RECEPTOR ANTAGONISTS

[75] Inventors: Francis D. King; Laramie M. Gaster, both of Bishop's Stortford; Paul A. Wyman, Epping, all of England

[73] Assignee: SmithKline Beecham p.l.c., Brentford, England

[21] Appl. No.: 204,428

[22] PCT Filed: Sep. 3, 1992

[86] PCT No.: PCT/GB92/01612

§ 371 Date: Nov. 14, 1994

§ 102(e) Date: Nov. 14, 1994

[87] PCT Pub. No.: WO93/05040

PCT Pub. Date: Mar. 18, 1993

[30] Foreign Application Priority Data

Sep. 12, 1991 [GB] United Kingdom .................. 9119449
Oct. 23, 1991 [GB] United Kingdom .................. 9122474
Jan. 23, 1992 [GB] United Kingdom .................. 9201413
Mar. 20, 1992 [GB] United Kingdom .................. 9206075

[51] Int. Cl.$^6$ .................. C07D 453/02; C07D 401/12; C07D 487/04; A16K 31/55
[52] U.S. Cl. .................. 514/214; 514/299; 514/306; 514/403; 514/413; 540/593; 546/112; 546/138; 546/183; 548/360.1; 548/455
[58] Field of Search .................. 514/306, 299, 514/214; 540/593; 546/138, 112, 183

[56] References Cited

U.S. PATENT DOCUMENTS

4,617,401 10/1986 Miyano et al. .................. 548/453

FOREIGN PATENT DOCUMENTS

0036269 9/1981 European Pat. Off. ...... C07D 455/02
59-184178 10/1984 Japan ............ C07D 487/04
84/00166 1/1984 WIPO.

OTHER PUBLICATIONS

Bockaert, J. et al. *Trends Pharmacol. Sci.* 13, 141–145 (1992).
Talley, N. J. *Aliment. Pharmacol. Ther.* 6, 273–289 (1992).
Sadykov, A. S et al. Chemical Abstract Service No. 100:156848 (1984).

Fessenden, R. J. et al. *Organic Chemistry* (Willard Grant Pr., Boston), p. 281 (1982).

Primary Examiner—Mukund J. Shah
Assistant Examiner—King Lit Wong
Attorney, Agent, or Firm—Charles M. Kinzig; Stephen Venetianer; Edward T. Lentz

[57] ABSTRACT

Compounds of formula (I),

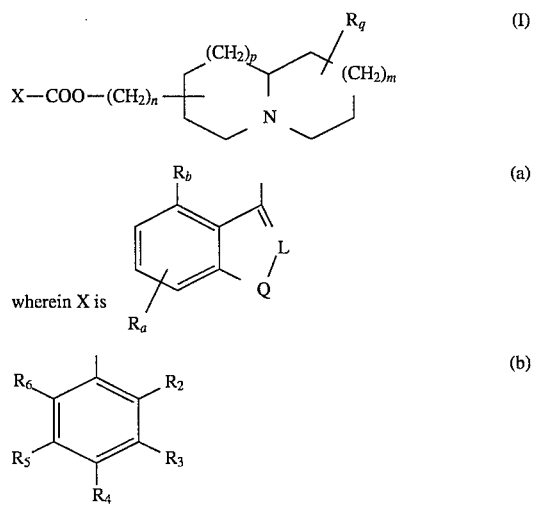

wherein L is N or $CR_c$, wherein $R_c$ is hydrogen, alkoxy, halo, alkyl or cyano; Q is $NR_1$, $CH_2$, O, or S; $R_a$ is hydrogen, halo, alkyl, amino, nitro or alkoxy; $R_b$ is hydrogen, halo, alkyl or alkoxy; $R_1$ is hydrogen, alkyl, alkenyl, aralkyl, alkanoyl, or alkanoylalkyl; $R_2$ is alkoxy; $R_3$ is hydrogen, chloro or fluoro; $R_4$ is hydrogen, alkyl, amino optionally substituted by alkyl, halo, hydroxy or alkoxy; $R_5$ is hydrogen, halo, alkyl, alkoxy, nitro, amino or alkylthio; $R_6$ is hydrogen, halo, alkyl, alkoxy or amino; n is 0, 1, 2, 3, or 4; p and m are independently 0, 1 or 2; and $R_q$ is hydrogen or $C_{1-6}$ are 5-HT$_4$ receptor antagonists.

15 Claims, No Drawings

AZABICYCLIC COMPOUNDS AS 5-HT4 RECEPTOR ANTAGONISTS

This invention relates to novel compounds having pharmacological activity, to a process for their preparation and to their use as pharmaceuticals.

GB 2125398A (Sandoz Limited) describes a group of bridged piperidinyl ester and amide derivatives having 5-HT$_3$ receptor antagonist activity. GB 1593146 and EP-A-36269 (Beecham Group p.l.c.) fused azabicyclic amide derivatives having gastric motility enhancing activity.

A class of novel, structurally distinct compounds has not been discovered, which compounds are fused azabicyclic ester derivatives. These compounds have 5-HT$_4$ receptor antagonist activity.

European Journal of Pharmacology 146 (1988) 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205-930, which is also a 5-HT$_3$ receptor antagonist, acts as an antagonist at this receptor.

PCT/GB9/00650 (SmithKline and French Laboratories Limited) describes the use of cardiac 5-HT$_4$ receptor antagonists in the treatment of atrial arrhythmias and stroke.

Accordingly, the present invention provides a compound of formula (I), or a pharmaceutically acceptable salt thereo

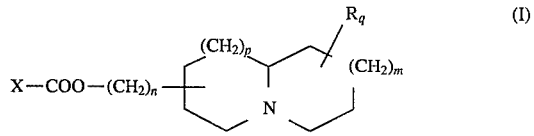

wherein
X is of sub-formula (a) or (b):

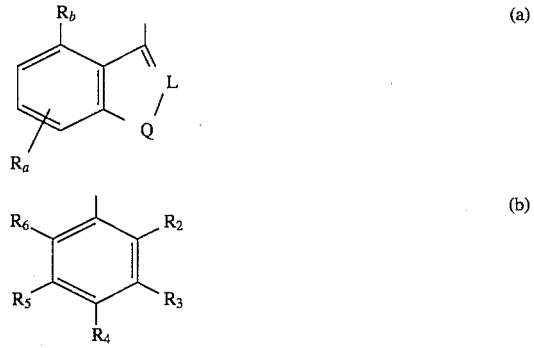

wherein
L is N or CR$_c$ wherein R$_c$ is hydrogen, C$_{1-6}$alkoxy, halo, C$_{1-6}$ alkyl or cyano;
Q is NR$_1$, CH$_2$, O or S;
R$_a$ is hydrogen, halo, C$_{1-6}$alkyl, amino, nitro or C$_{1-6}$alkoxy;
R$_b$ is hydrogen, halo, C$_{1-6}$alkyl or C$_{1-6}$alkoxy;
R$_1$ is hydrogen, C$_{1-10}$alkyl, C$_{2-6}$alkenyl, aralkyl, C$_{2-6}$alkanoyl, or C$_{2-6}$ alkanoyl C$_{1-3}$alkyl;
R$_2$ is C$_{1-6}$alkoxy; and
R$_3$ is hydrogen, chloro or fluoro;
R$_4$ is hydrogen, C$_{1-6}$alkyl, amino optionally substituted by a C$_{1-6}$alkyl group, halo, hydroxy or C$_{1-6}$alkoxy;
R$_5$ is hydrogen, halo, C$_{1-6}$alkyl, C$_{1-6}$alkoxy, nitro, amino or C$_{14-6}$alkylthio;
R$_6$ is hydrogen, halo, C$_{1-6}$alkyl, C$_{1-6}$alkoxy or amino;
n is 0, 1, 2, 3 or 4;
p and m are independently 0, 1 or 2; and
R$_q$ is hydrogen or C$_{1-6}$alkyl.

Examples of alkyl or alkyl containing groups include C$_1$, C$_2$, C$_3$, C$_4$, C$_5$, C$_6$, C$_7$, C$_8$, C$_9$ or C$_{10}$ branched, straight chained or cyclic alkyl, as appropriate. C$_{1-4}$ alkyl groups include methyl, ethyl n- and iso-propyl, n-, iso-, sec- and tert-butyl. Cyclic alkyl includes cyclopropyl, cyclobutyl, cyclopentyl, cyclohexyl, cycloheptyl and cyclooctyl. Alkenyl includes all suitable values including E and Z forms.

Aryl includes phenyl and naphthyl optionally substituted by one or two substituents selected from halo, C$_{1-6}$ alkoxy and C$_{1-6}$ alkyl.

Halo includes fluoro, chloro, bromo and iodo.

L in formula (a) is preferably CH, C—CH$_3$, C—Cl or COCH$_3$.

Q in formula (a) is preferably NR$_1$ and R$_1$ is preferably hydrogen or a methyl or ethyl group.

R$_a$ is often hydrogen and R$_b$ is often hydrogen or iodo.
R$_2$ is preferably methoxy.
R$_4$ is preferably amino.
R$_5$ when halo is selected from fluoro, chloro, bromo and iodo, preferably chloro.

Suitable values for p and m include p=m=1; p=0, m=1; p=1, m=2; p=2, m=1.

R$_q$ is often hydrogen.

Preferably X—COO—(CH$_2$)$_n$— is attached such that the number of carbon atoms between the ester linkage and the azabicydic nitrogen atom is from 2 to 4 carbon atoms.

Specific values of the azabicylic which are of particular interest are as follows:

(i)

(ii)

(iii)

Other azacycles of interest are as described with reference to the Examples.

The pharmaceutically acceptable salts of the compounds of the formula (I) include acid addition salts with conventional acids such as hydrochloric, hydrobromic, boric, phosphoric, sulphuric acids and pharmaceutically, acceptable organic acids such as acetic, tartaric, maleic, citric, succinic, benzoic, ascorbic, methanesulphonic, a-keto glutaric, a-glycerophosphoric, and glucose-1-phosphoric acids.

Examples of pharmaceutically acceptable salts include quaternary derivatives of the compounds of formula (I) such as the compounds quaternised by compounds R$_x$—T wherein R$_x$ is C$_{1-6}$ alkyl, phenyl-C$_{1-6}$ alkyl or C$_{5-7}$ cycloalkyl, and T is a radical corresponding to an anion of an acid. Suitable examples of R$_x$ include methyl, ethyl and n- and iso-propyl; and benzyl and phenethyl. Suitable examples oft include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

Some of the compounds of formula (I) have at least one asymmetric centre and exist as more than one stereoisomeric form. The invention extends to each of these forms and to mixtures thereof including racemates.

It will also be realised that X—COO—(CH$_2$)$_n$— in compounds of formula (I) may adopt an α or β or configuration with respect to the fused azabicydic moiety.

The compounds of formula (I) are prepared by linking together X—CO$_2$H or a reactive derivative thereof and the (azabicydic side chain)—(CH$_2$)$_n$— moiety, usually by a conventional ester coupling with the —(CH$_2$)$_n$—OH derivative as described in the aforementioned patent publication reference in the name of Sandoz Limited.

The azabicydic side chain (CH$_2$)$_n$—OH intermediates are known compounds or may be prepared from the ketones of formula (II):

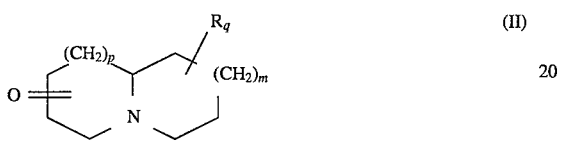

according to conventional methods, such as those described in the Descriptions hereinafter.

Ketones of the formula (II) are known or are prepared by analogous methods to those used for preparing structurally related known compounds.

The compounds of the present invention are 5-HT$_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-HT$_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

It is believed that platelet-derived 5-HT induces atrial arrhythmias which encourage atrial fibrillation and atrial disorders are associated with symptomatic cerebral and systemic embolism. Cerebral embolism is the most common cause of ischaemic stroke and the heart the most common source of embolic material. Of particular concern is the frequency of embolism associated with atrial fibrillation.

Anxiolytic activity is likely to be effected via the hippocampus (Dumuis et al 1988, Mol. Pharmacol., 34, 880–887). Activity may be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-HT$_4$ receptors, and hence that administration of a 5-HT$_4$ antagonist is of potential benefit in relieving a migraine attack.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral,nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Sublingual or transdermal administration is also envisaged. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment of irritable bowel syndrome, gastro-oesophagal reflux disease, dyspepsia, atrial arrhythmias and stroke, anxiety and/or migraine in mammals, such as humans, which comprises the administration of an effective amount of a compound of the formula (I) or a pharmaceutically acceptable salt thereof. In particular, the method comprises treatment of IBS or atrial arrhythmias and stroke.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophagal reflux disease, dyspepsia, atrial arrhythmias and stroke, anxiety and/or migraine, in particular IBS or atrial arrhythmias and stroke.

The invention also provides the use of a compound of formula (I) in the manufacture of a medicament for use as a 5-HT$_4$ receptor antagonist in the treatment of irritable bowel syndrome, gastro-oesophagal reflux disease, dyspepsia, atrial arrhythmias and stroke, anxiety and/or migraine, in particular, IBS or atrial arrhythmias and stroke.

The following Examples illustrate the preparation of compounds of formula (I); the following Descriptions illustrate the preparation of intermediates.

EXAMPLES

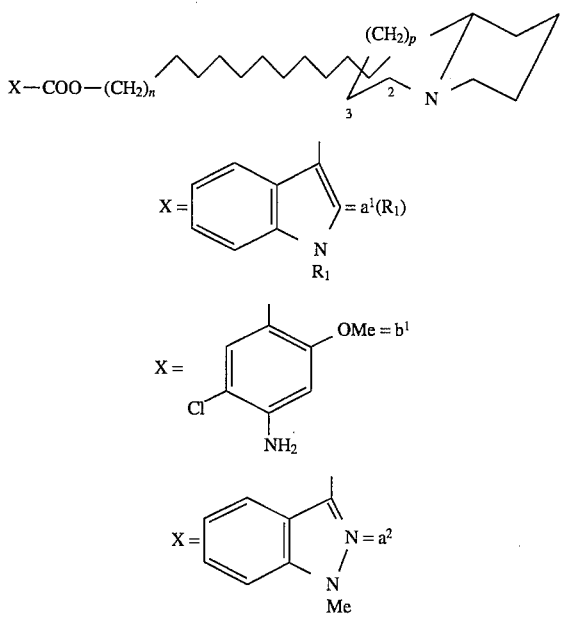

| Example | X | n | p | attach. | isomer(s) |
|---|---|---|---|---|---|
| E1 | a$^1$(H) | 1 | 1 | 3 | α,β |
| E2 | a$^1$(H) | 2 | 1 | 3 | |
| E3 | a$^1$(H) | 0 | 1 | 3 | α,β |
| E4 | a$^1$(H) | 0 | 1 | 4 | α,β |
| E5 | a$^1$(H) | 1 | 0 | 3 | α,β |
| E6 | a$^1$(H) | 2 | 0 | 3 | α,β |
| E7 | a$^2$ | 1 | 1 | 3 | α,β |
| E8 | b$^1$ | 1 | 1 | 3 | α,β |
| E9 | a$^1$(H) | 1 | 1 | 4 | α,β |
| E10 | a$^1$(H) | 2 | 1 | 4 | β |
| E11 | a$^1$(H) | 0 | 1 | 5 | α,β |
| E12 | a$^1$(H) | 1 | 1 | 5 | α,β |
| E13 | a$^1$(H) | 0 | 0 | 4 | α,β |
| E14 | a$^1$(H) | 1 | 0 | 4 | α,β |
| E15 | a$^1$(Me) | 1 | 1 | 4 | β |
| E16 | a$^1$(Et) | 1 | 1 | 4 | β |
| E17 | a$^1$($^n$Pr) | 1 | 1 | 4 | β |
| E18 | a$^1$($^i$Pr) | 1 | 1 | 4 | β |
| E19 | a$^1$(allyl) | 1 | 1 | 4 | β |
| E20 | a$^1$($^i$Bu) | 1 | 1 | 4 | β |
| E21 | a$^1$(Me) | 1 | 0 | 3 | α,β |
| E22 | a$^1$(Et) | 1 | 0 | 3 | α,β |
| E23 | a$^1$($^n$Pr) | 1 | 0 | 3 | α,β |
| E24 | a$^1$(H) | 1 | 2 | 4 | α,β |
| E25 | a$^1$(H) | 1 | 2 | 5 | α,β |
| E26 | a$^1$(H) (R$_c$ = OCH$_3$) | 1 | 1 | 4 | β |
| E27 | a$^1$($^i$Pr) (R$_b$ = 1) | 1 | 1 | 4 | β |
| E28 | a$^1$(cpm) | 1 | 1 | 4 | β |
| E29 | a$^1$(chm) | 1 | 1 | 4 | β |
| E30 | a$^1$(COCH$_3$) | 1 | 1 | 4 | β |
| E31 | a$^1$(CH$_2$Ac) | 1 | 1 | 4 | β |
| E32 | a$^1$($^n$Pr) | 1 | 0 | 3 | α,β* | cpm = cyclopropylmethyl
chm = cyclohexylmethyl
* = N-methyl iodide quaternary salt

Example 1

3-ax- and 3-eq-Quinolizidin-3-ylmethylindole-3-carboxylate (E1a and E1b)

A suspension of indole-3-carboxylic acid (400 mg, 0.0025 mole) in dichloromethane (25 ml) was treated with oxalyl chloride (0.24 ml, 0.0028 mole) plus 2 drops of DMF and stirred at room temperature for 2 hours, then concentrated in vacuo to give the acid chloride as a yellow solid. A solution of 3-hydroxymethylquinolizidine (H. Lewis and C. Shoppee J.C.S., 1956, 313) (mixture of isomers) (435 mg, 0.0025 mole) in THF (10 ml) at 5° C. under nitrogen was treated with 1.6M n-butyllithium in hexane (1.56 ml, 0.0025 ml), stirred for 10 minutes, then treated with a solution of the above acid chloride in THF (5 ml). After 2 hours at room temperature, the mixture was treated with saturated $NaHCO_3$ solution (20 ml) and extracted with ethyl acetate (2×30 ml). The combined extracts were dried ($Na_2SO_4$), concentrated in vacuo and the residue chromatographed on silica gel. The faster running component was obtained by elution with ethyl acetate and afforded the axial isomer (E1a) as a white solid mp 157°–158° C.

$^1$H NMR (CDCl$_3$)

δ: 1.20–2.28 (m,14H), 2.68–2.79 (m,1H), 2.85–2.96 (m,1H), 4.45–4.60 (m, 2H), 7.21–7.30 (m,2H), 7.37–7.45 (m,1H), 7.91 (d, 1H), 8.13–8.20 (m,1H), 9.40 (br.s, 1H).

MS (EI) M$^+$312

Elution with ethyl acetate:methanol (9:1) afforded the equatorial isomer (E1b) as a white solid mp 187°–188° C.

$^1$H NMR (CDCl$_3$)

δ: 1.07–1.50 (m,4H), 1.53–2.15 (m,9H), 2.15–2.37 (m,1H), 2.82–2.93 (m, 1H), 3.07–3.17 (m,1H), 4.18 (d, 2H), 7.22–7.30 (m,2H), 7.40–7.50 (m,1H), 7.90 (d, 1H), 8.15–8.23 (m,1H), 9.65 (br.s, 1H).

MS (EI) M$^+$312

Example 2

3-ax- and 3-eq-Quinolizidin-3-ylethylindole-3-carboxylate (E2a and E2b)

The title compounds were prepared from 3-(2-hydroxyethyl)quinolizidine (D1) (mixture of isomers) and indole-3-carboxylic acid chloride using the method of Example 1. The isomers were separated by chromatography on silica gel eluting with ethyl acetate. Pooling of the fractions containing the faster running component afforded the axial isomer (E2a) as a colourless oil, which was converted to its hydrochloride salt mp 207°–209° C. (acetone).

Free base: $^1$H NMR (CDCl$_3$)

δ: 1.15–1.80 (m,11H), 1.85–2.25 (m,5H), 2.65–2.80 (m,2H), 4.36 (t,2H, J=7Hz), 7.20–7.30 (m,2H), 7.35–7.45 (m,1H), 7.87 (d, 1H), 8.10–8.18 (m, 1H), 9.30 (br.s, 1H).

MS (Cl) MH$^+$327

Fractions containing the lower running component afforded the equatorial isomer (E2b) as a colourless oil, which was converted to its hydrochloride salt mp. 224°–225° C. (acetone).

Free base: $^1$H NMR (CDCl$_3$)

δ: 0.90–1.45 (m,5H), 1.45–2.12 (m,11H), 2.78–2.98 (m,2H), 4.35 (t,2H, J=7Hz), 7.15–7.25 (m,2H), 7.32–7.42 (m,1H), 7.68 (d, 1H), 8.10–8.18 (m, 1H) and 10.0 (br.s, 1H).

MS (Cl) MH$^{30}$ 327

Example 3

3-ax- and 3-eq-Quinolizidin-3-ylindole-3-carboxylate (E3a and E3b)

3-Hydroxyquinolizidine (C. Rader et al., J. Org. Chem., 1964, 29, 2252) (mixture of isomers) was reacted with indole-3-carboxylic acid chloride using the method of Example 1. The product was chromatographed on silica gel eluting with ether. The faster running component proved to be the axial isomer (E3a), obtained as a white solid mp 202°–204° C.

$^1$H NMR (CDCl$_3$)

δ: 1.20–2.60 (m,13H), 2.86–3.00 (m,1H), 3.33–3.45 (m,1H), 5.21 (br.s, 1H), 6.94–7.10 (m,2H), 7.16–7.25 (m,1H), 7.52 (d, 1H), 7.82–7.90 (m,1H) and 11.35 (br.s, 1H).

MS (Cl) MH$^+$299

The slower running component was the equatorial isomer (E3b) obtained as a beige solid mp 199°–202° C. (ethyl acetate/petrol).

$^1$H NMR (CDCl$_3$)

δ: 1.19–1.40 (m,2H), 1.40–2.33 (m,11H), 2.82–2.93 (m,1H), 3.16–3.27 (m, 1H), 5.10–5.24 (m,1H), 7.20–7.30 (m,2H), 7.38–7.46 (m,1H), 7.93 (d, 1H), 8.10–8.18 (m,1H), 8.95 (br.s, 1H).

MS (Cl) MH$^+$299

Example 4

2-ax- and 2-eq-Quinolizidin-2-ylindole-3-carboxylate (E4a and E4b)

2-Hydroxyquinolizidine (C. Rader et al., J. Org. Chem., 1964, 29, 2252) (mixture of isomers) was reacted with indole-3-carboxylic acid chloride using the method of Example 1. The yellow oil obtained was treated with ether and the equatorial isomer (E4b) precipitated out as a white solid mp 215°–216° C. (ethyl acetate/petrol).

$^1$H NMR (d$^6$DMSO)

δ: 1.18–2.23 (m,13H), 2.80–2.95 (m,2H), 4.84–5.00 (m,1H), 7.22–7.35 (m, 2H), 7.53–7.60 (m,1H), 8.04–8.10 (m,1H), 8.15 (s, 1H), 12.0 (br.s, 1H).

MS (EI) M$^+$298

The material contained in the filtrate was chromatographed on silica gel eluting with ethyl acetate and the fractions containing the slower running product afforded the axial isomer (E4a) as a white solid mp 67°–72° C.

$^1$H NMR (CDCl$_3$)

δ: 1.20–1.43 (m,2H), 1.48–1.85 (m,5H), 1.90–2.40 (m,5H), 2.52–2.67 (m, 1H), 2.71–2.83 (m,1H), 2.87–2.98 (m,1H), 5.35–5.43 (m,1H), 7.23–7.37 (m, 2H), 7.39–7.48 (m,1H), 7.96 (d, 1H), 8.18–8.27 (m,1H), 8.97 (br.s, 1H).

MS (EI) M$^+$298

Example 5 cis-2,9-H- and trans-2,9-H-Indolizidin-2-ylmethylindole-3-carboxylate (E5a and E5b)

2-Hydroxymethylindolizidine (K. Winterfield et al., Arch. Pharm., 1958, 291,485) (mixture of isomers) was reacted with indole-3-carboxylic acid chloride using the method of Example 1. The isomers were separated by chromatography on silica gel eluting with ethyl acetate:methanol (98:2). The faster running component gave the cis isomer E5a as a colourless oil and converted to its hydrochloride salt mp 191°–194° C. (acetone).

HCl salt: $^1$NMR (d$^6$DMSO)

δ: 1.30–2.10 (m,7H), 2.28–2.45 (m,1H), 2.74–2.96 (m,2H), 3.04–3.25 (m, 2H), 3.35–3.56 (m,2H), 4.34 (d, 2H), 7.14–7.26 (m,2H), 7.45–7.55 (m,1H), 7.90–8.00 (m,1H), 8.18 (d, 1H), 10.95 (br.s, 1H) and 12.10 (br.s, 1H).

MS (EI) M$^+$298

The slower running component gave the trans isomer E5b as a colourless oil and converted to its hydrochloride salt, mp 199°–201° C. (acetone).

HCl salt: $^1$H NMR (d$^6$DMSO)

δ: 1.32–1.50 (m,1H), 1.55–2.15 (m,8H), 2.75–2.95 (m,2H), 3.10–3.27 (m, 1H), 3.45–3.54 (m,1H), 3.60–3.70 (m,1H), 4.18–4.37 (m,2H), 7.17–7.24 (m, 2H), 7.47–7.54 (m,1H), 7.92–7.99 (m,1H), 8.14 (d, 1H), 10.95 (br.s, 1H) and 12.15 (br.s, 1H).

MS (EI) M$^+$298

Example 6 cis-2,9-H- and trans-2,9-H-Indolizidin-2-ylethylindole-3-carboxylate (E6)

A mixture of the title compounds was prepared from 2-(2-hydroxyethyl)indolizidine (K. Winterfield et al., Arch. Pharm., 1958, 291, 485) (mixture of isomers) and indole-3-carboxylic acid chloride using the method of Example 1. The material was chromatographed on silica gel eluting with ethyl acetate:methanol (19:1), but the isomers were not separated. The colourless oil was converted to its hydrochloride salt, which proved to be a hygroscopic white solid mp 45°–50° C. $^1$H NMR showed a 3:2 mixture of isomers.

Free base: $^1$H NMR (CDCl$_3$)

δ: 1.10–1.35 and 1.45–2.45 (each m, together 14H), 2.85–2.95 (dd, 1H major isomer), 3.02–3.17 (m,1H), 3.26–3.35 (m,1H minor isomer), 4.33 (t,2H), 7.20–7.30 (m,2H), 7.37–7.45 (m,1H), 7.87 (d, 1H minor isomer), 7.90 (d, 1H major isomer), 8.12–8.23 (m,1H) and 9.60 (br.s, 1H).

MS (EI) M$^+$312

Example 7

3-ax- and 3-eq-Quinolizidin-3-ylmethyl-1-methylindazole-3-carboxylate (E7a and E7b)

The title compounds were prepared from 3-hydroxymethylquinolizidine (H. Lewis and C. Shoppee J. Chem. Soc., 1956, 313) (mixture of isomers) and 1-methylindazole-3-carboxylic acid chloride using the method of Example 1. The isomers were separated by chromatography on silica gel eluting with ethyl acetate. Fractions containing the faster running component afforded the axial isomer (E7a) as a colourless oil, which was converted to its hydrochloride salt mp 238°–239° C. (acetone).

Free base: $^1$H NMR (CDCl$_3$)

δ: 1.19–1.35 (m,2H), 1.38–2.03 (m,10H), 2.16–2.32 (m,2H), 2.65–2.75 (m, 1H), 2.80–2.90 (m,1H), 4.18 (s, 3H), 4.62–4.75 (m,2H), 7.29–7.37 (m,1H), 7.43–7.49 (m,2H), 8.19 (d, 1H).

MS (CI) MH$^+$328

Fractions containing the lower running component afforded the equatorial isomer (E7b) as a colourless oil, which was converted to its hydrochloride salt mp 199°–201° C. (acetone).

HCl salt: $^1$H NMR (d$^6$DMSO)

δ: 5:1.30–1.95 (m,11H), 2.73–3.05 (m,3H), 3.25–3.42 (m,2H), 4.18 (s, 3H), 4.22–4.35 (m,2H), 7.33–7.42 (m,1H), 7.48–7.57 (m,1H), 7.80 (d, 1H), 8.06 (d, 1H), 10.9 (br.s, 1H).

MS (Cl) MH$^{30}$ 328

Example 8

3-ax- and 3-eq-Quinolizidin-3-ylmethyl-4-amino-5-chloro-2-methoxybenzoate (E8a and E8b)

A solution of 4-amino-5-chloro-2-methoxybenzoic acid (500 mg, 0.0025 mole) in acetonitrile (30 ml) was treated with N,N'-carbonyldiimidazole (400 mg, 0.0025 mole) and stirred at room temperature under nitrogen for hours, then concentrated in vacuo to give a yellow oil containing the imidazolide. A solution of 3-hydroxymethylquinolizidine (H. Lewis and C. Shoppee J. Chem. Soc., 1956, 313) (mixture of isomers) (425 mg, 0.0025 mole) in THF (20 ml) at 5° C. under nitrogen was treated with 1.6M n-butyllithium in hexane (1.6 ml, 0.0025 mole), stirred for 10 minutes, then treated with the above imidazolide. After 16 hours at room temperature, the mixture was treated with 10% Na$_2$CO$_3$ solution (20 ml) and extracted with ethyl acetate (2×30 ml). The combined extracts were dried (Na$_2$SO$_4$), concentrated in vacuo and the residue chromatographed on silica gel eluting with ethyl acetate:ether (1:1). Fractions containing the faster running component afforded the axial isomer (E8a) as a white solid mp 158°–161° C.

$^1$H NMR (CDCl$_3$+D$_2$O)

δ: 1.18–2.00 (m,12H), 2.05–2.22 (m,2H), 2.65–2.85 (m,2H), 3.84 (s, 3H), 4.38–4.50 (m,2H), 4.80 (br.s, 2H), 6.30 (s, 1H), 7.83 (s, 1H).

MS (Cl) MH$^+$353

Fractions containing the lower running component afforded the equatorial isomer (E8b) as a white solid mp 92°–96° C.

$^1$H NMR (CDCl$_3$)

δ: 1.10–1.55 (m,4H), 1.65–2.35 (m,10H), 2.90–3.00 (m,1H), 3.05–3.15 (m, 1H), 3.94 (s, 3H), 4.05–4.28 (m,2H), 4.55 (br.s, 2H), 6.38 (s, 1H), 7.90 (s, 1H).

Example 9 a) ax-Quinolizidin-2-ylmethylindole-3-carboxylate (E9a)

The title compound was prepared from ax-2-hydroxymethylquinolizidine (D4) and indole-3-carboxylic acid chloride using the method of Example 1. The product was purified by chromatography on neutral alumina eluting with ethyl acetate, followed by crystallisation from ether/pentane, to give the title compound (E9a) as a white solid mp 156°–157° C.

$^1$H NMR (CDCl$_3$)

δ: 9.40 (br.s, 1H), 8.10–8.20 (m,1H), 7.93 (d, 1H), 7.37–7.45 (m,1H), 7.22–7.33 (m,2H), 4.35–4.50 (m,2H), 2.77–2.93 (m,1H), 2.63–2.75 (m,1H), 2.23–2.43 (m,2H), 1.43–2.20 (m,10H), 1.17–1.40 (m,2H).

MS (EI) M⁺312 b) eq-Quinolizidin-2-ylmethylindole-3-carboxylate (E9b)

The title compound was prepared from eq-2-hydroxymethylquinolizidine (N. J. Leonard et al, J. Org. Chem., 1957, 22, 1445) and indole-3-carboxylic acid chloride using the method of Example 1. The yellow oil obtained was crystallised from ether to afford the title compound (E9b) as a beige solid mp 154°–157° C.

$^1$H NMR (CDCl$_3$)

δ: 9.40 (br.s,1H), 8.10–8.20 (m,1H), 7.87 (d, 1H), 7.35–7.45 (m,1H), 7.20–7.30 (m,2H), 4.20 (d,2H), 2.80–2.97 (m,2H), 1.43–2.20 (m,11H), 1.10–1.40 (m,3H).

MS (EI) M⁺312

Example 10 eq-Quinolizidin-2-ylethylindole-3-carboxylate (E10)

eq-2-(2-Hydroxyethyl)quinolizidine (D5) was reacted with indole-3-carboxylic acid chloride using the method of Example 1. The product was chromatographed on silica gel eluting with ethyl acetate/methanol (95:5). The resulting beige solid was recrystallised from ethyl acetate/petrol (60–80) to afford the title compound (E10) as a white solid mp 170°–172° C.

$^1$H NMR (CDCl$_3$)

δ: 9.15 (br.s, 1H), 8.12–8.22 (m,1H), 7.91 (d, 1H), 7.36–7.45 (m,1H), 7.20–7.30 (m,2H), 4.38 (t,2H), 2.80–2.92 (m,2H), 1.93–2.17 (m,3H), 1.20–1.83 (m,12H), 1.00–1.18 (m,1H).

MS (EI) M⁺326

Example 11 a) eq-Quinolizidin-1-ylindole-3-carboxylate (E11a)

eq-1-Hydroxyquinolizidine (H. S. Aaron et al, J. Org. Chem. 1964, 29, 2248) was reacted with indole-3-carboxylic acid chloride using the method of Example 1. The product was chromatographed on silica gel eluting with ether to afford the title compound (E11a) as a white solid, mp 230°–232° C.

$^1$H NMR (CDCl$_3$)

δ: 8.88 (br.s,1H), 8.11–8.20 (m,1H), 7.93 (d, 1H), 7.38–7.46 (m,1H), 7.22–7.32 (m,2H), 4.80–4.94 (m,1H), 2.75–2.98 (m,2H), 1.92–2.32 (m,5H), 1.38–1.88 (m,6H), 1.15–1.35 (m,2H).

MS (CI) MH⁺299 b) ax-Quinolizidin-1-ylindole-a-carboxylate (E11b)

ax-1-Hydroxyquinolizidine (H. S. Aaron et al, J. Org. Chem., 1964, 29, 2248) was reacted with indole-3-carboxylic acid chloride using the method of Example 1. The product was chromatographed on silica gel eluting with ether, followed by trituration with ether, to afford the title compound (E11b) as a white solid mp 80°–85° C.

$^1$H NMR (CDCl$_3$)

δ: 9.75 (br.s, 1H), 8.27–8.36 (m,1H), 7.83 (d, 1H), 7.17–7.45 (m,3H), 5.20 (s,1H), 2.90–3.05 (m,2H), 1.15–2.30 (m,13H).

MS (EI) MH⁺299

Example 12 ax-and eq-Quinolizidin-1-ylmethylindole-3-carboxylate (E12a and E12b)

1-Hydroxymethylquinolizidine (G. R. Clemo et al, J. Chem. Soc., 1937, 965 and 1938, 1574) (mixture of isomers) was reacted with indole-3-carboxylic acid chloride using the method of Example 1. The isomers were separated by chromatography on silica gel eluting with ethyl acetate/methanol (97:3). Fractions containing the faster running component afforded the axial isomer (E12a) as a white solid mp 173°–177° C.

$^1$H NMR (CDCl$_3$)

δ: 9.75 (br.s, 1H), 8.12–8.23 (m,1H), 7.92 (s,1H), 7.36–7.47 (m,1H), 7.20–7.32 (m,2H), 4.60–4.72 (m,1H), 4.40–4.53 (m,1H), 2.80–2.95 (m,2H), 1.15–2.25 (m,14H).

MS (EI) M⁺312

Combining fractions containing the slower running component gave the equatorial isomer (E12b) as a white solid mp 55°–60° C.

$^1$H NMR (CDCl$_3$)

δ: 10.35 (br.s,1H), 8.15–8.25 (m,1H), 7.94 (d, 1H), 7.37–7.47 (m,1H), 7.22–7.32 (m,2H), 4.22–4.43 (m,2H), 2.83–2.97 (m,2H), 1.50–2.20 (m,11H), 1.20–1.46 (m,3H).

MS (CI) MH⁺313

Example 13 cis-1,9-H- and trans-1,9-H-Indolizidin-1-ylindole-3-carboxylate (E13a and E13b)

1-Hydroxyindolizidine (H. S. Aaron, J. Org. Chem., 1966, 31, 3502) (mixture of isomers) was reacted with indole-3-carboxylic acid chloride using the method of Example 1. The isomers were separated by chromatography on silica gel eluting with ether. The faster running component was obtained as a white solid mp 169°–170° C.

$^1$H NMR (CDCl$_3$)

δ: 8.85 (br.s, 1H), 8.10–8.20 (m,1H), 7.95 (d, 1H), 7.39–7.50 (m,1H), 7.20–7.35 (m,2H), 5.05–5.20 (m,1H), 3.00–3.20 (m,2H), 1.20–2.65 (m,11H).

MS (CI) MH⁺285

The slower running component was obtained as a white solid mp 179°–181° C.

$^1$H NMR (CDCl$_3$)

δ: 10.70 (br.s,1H), 8.20–8.35 (m,1H), 8.10 (br.s, 1H), 7.35–7.45 (m,1H), 7.20–7.33 (m,2H), 5.63–5.75 (m,1H), 3.25–3.50 (m,2H), 2.35–2.50 (m,1H), 2.35–2.50 (m,1H), 1.50–2.30 (m,9H), 1.20–1.45 (m,1H).

MS (CI) MH⁺285

Example 14 cis-1,9-H-Indolizidin-1-ylmethylindole-3-carboxylate (E14a)

cis-1,9-H-1-Hydroxymethylindolizidine (D6a) was reacted with indole-3-carboxylic acid chloride using the method of Example 1. The product was chromatographed on silica gel eluting with ethyl acetate/methanol (19:1) to afford a colourless oil, which was crystallised from ether to give E14a as a white solid mp 140°–141° C.

$^1$H NMR(CDCl$_3$)

δ: 9.00 (br.s, 1H), 8.15–8.25 (m,1H), 7.90 (d,1H), 7.37–7.45 (m,1H), 7.20–7.30 (m,2H), 4.40–4.50 (dd, 1H), 4.08–4.20 (dd,1H), 3.00–3.20 (m,2H), 2.50–2.68 (m,1H), 1.35–2.15 (m,10H), 1.10–1.30 (m,1H).

MS (EI) M$^+$298 trans-1,9-H-Indolizidin-1-ylmethylindole-3-carboxylate (E14b)

trans-1,9-H-1-Hydroxymethylindolizidine (D6b) was reacted with indole-3-carboxylic acid chloride using the method of Example 1. The product was chromatographed on silica gel eluting with ethyl acetate/methanol (19:1) followed by crystallisation from ether to afford the title compound (E14b) as a white solid mp 116°–118° C.

$^1$H NMR (CDCl$_3$)

δ: 9.30 (br.s,1H), 8.12–8.23 (m,1H), 7.90 (d,1H), 7.37–7.47 (m,1H), 7.22–7.33 (m,2H), 4.28–4.40 (m,2H), 3.05–3.18 (m,2H), 1.95–2.35 (m,5H), 1.47–1.85 (m,5H), 1.13–1.43 (m,2H).

MS (EI) M$^+$298

Example 15 eq-Quinolizidin-2-ylmethyl-1-methylindole-3-carboxylate (E15)

eq-2-Hydroxymethylquinolizidine (N. J. Leonard et al, J. Org. Chem., 1957, 22, 1445) was reacted with the acid chloride of 1-methylindole-3-carboxylic acid using the method of Example 1. The product was chromatographed on silica gel eluting with ethyl acetate. The resulting pale yellow oil was crystallised from n-pentane to afford the title compound (E15) as a white crystalline solid mp 115°–116° C.

$^1$H NMR (CDCl$_3$)

δ: 8.12–8.20 (m,1H), 7.80 (s,1H), 7.23–7.38 (m,3H), 4.18 (d,2H), 3.84 (s,3H), 2.80–2.93 (m,2H), 1.42–2.15 (m,11H), 1.08–1.35 (m,3H).

MS (EI) M$^+$326

Example 16 eq-Quinolizidin-2-ylmethyl-1-ethylindole-3-carboxylate (E16)

eq-2-Hydroxymethylquinolizidine (N. J. Leonard et al, J. Org. Chem., 1957, 22, 1445) was reacted with the acid chloride of 1-ethylindole-3-carboxylic acid using the method of Example 1. The product was chromatographed on silica gel eluting with ethyl acetate to afford the title compound (E16) as a pale yellow oil. This was converted to its hydrochloride salt mp 168°–172° C.

$^1$H NMR (HCl salt) (CDCl$_3$)

δ: 12.10 (br.s,1H), 8.14 (s,1H), 8.07–8.18 (m,1H), 7.35–7.43 (m,1H), 7.23–7.32 (m,2H), 4.18–4.28 (d,2H and q,2H), 3.38–3.55 (m,2H), 2.30–2.83 (m,5H), 2.00–2.22 (m,3H), 1.75–2.00 (m,5H), 1.55 (t,3H), 1.35–1.60 (m,1H).

MS (EI) M$^+$340

Example 17 eq-Quinolizidin-2-ylmethyl-1-n-propylindole-3-carboxylate (E17)

eq-2-Hydroxymethylquinolizidine (N. J. Leonard et al, J. Org. Chem.,1957, 22, 1445) was reacted with the acid chloride of 1-n-propylindole-3-carboxylic acid using the method of Example 1. The product was chromatographed on silica gel eluting with ethyl acetate. The resulting yellow oil was crystallised from n-pentane to afford the title compound (E17) as a white solid mp 75°–76° C.

$^1$H NMR (CDCl$_3$)

δ: 8.12–8.20 (m,1H), 7.84 (s, 1H), 7.33–7.42 (m,1H), 7.23–7.32 (m,2H), 4.18 (d,2H), 4.10 (t,2H), 2.80–2.95 (m,2H), 1.42–2.15 (m,13H), 1.06–1.36 (m,3H), 0.95 (t,3H).

MS (EI) M$^+$354

Example 18 eq-Quinolizidin-2-ylmethyl-1-isopropylindole-3-carboxylate (E18)

A solution of eq-quinolizidin-2-ylmethylindole-3-carboxylate (E9b) (320 mg, 1.08 mmole) in dry THF (15 ml) at room temperature under nitrogen was treated with potassium t-butoxide (125 mg, 1.1 mmole) and stirred for 20 minutes. The solution was then treated with 2-iodopropane (0.11 ml, 1.1 mmole) and stirred for 18 h. The reaction mixture was treated with 10% Na$_2$CO$_3$ solution (25 ml) and extracted with ethyl acetate (2×50 ml). The combined extracts were dried (Na$_2$SO$_4$), concentrated in vacuo and the residue chromatographed on silica gel eluting initially with ether, then with ethyl acetate, to afford the title compound (E18) as a colourless oil (240 mg, 63%). This was converted to the hydrochloride salt mp 235°–238° C. (acetone).

$^1$H NMR (HCl salt) (d$^6$DMSO)

δ: 10.60 (br.s,1H), 8.32 (s,1H), 8.00–8.05 (m,1H), 7.62–7.67 (m,1H), 7.20–7.30 (m,2H), 4.84 (septet, 1H), 4.15 (d,2H), 3.25–3.40 (m,2H), 2.77–3.12 (m,3H), 2.05–2.18 (m,1H), 1.70–1.95 (m,7H), 1.55–1.70 (m,2H), 1.53 (d,6H), 1.40–1.52 (m,1H).

MS (EI) $^+$354

Example 19 eq-Quinolizidin-2-ylmethyl-1-allylindole-3-carboxylate (E19)

eq-Quinolizidin-2-ylmethylindole-3-carboxylate (E9b) was alkylated with allyl iodide using the method in Example 18. The product was chromatographed on silica gel eluting initially with ether, then with ethyl acetate, to afford the title compound (E19) as a colourless oil. This was converted to its hydrochloride salt mp 190°–192° C. (acetone)

$^1$H NMR (HCl salt) (d$^6$DMSO)

δ: 10.45 (br.s, 1H), 8.26 (s,1H), 7.98–8.05 (m,1H), 7.52–7.57 (m,1H), 7.20–7.28 (m,2H), 5.98–6.10 (m,1H), 5.20 (d,1H,J=10 Hz), 5.10 (d,1H,J=16 Hz), 4.93 (d,2H,J=6 Hz), 4.14 (d,2H), 3.25–3.38 (m,2H), 2.77–3.13 (m,3H), 2.04–2.17 (m,1H), 1.70–1.95 (m,7H), 1.37–1.68 (m,3H).

MS (EI) M$^+$352

Example 20 eq-Quinolizidin-2-ylmethyl-1-isobutylindole-3-carboxylate (E20)

eq-Quinolizidin-2-ylmethylindole-3-carboxylate (E9b) was alkylated with 1-bromo-2-methylpropane using the method in Example 18. The product was chromatographed on silica gel eluting initially with ether, then with ethyl acetate, to afford the title compound (E20) as a colourless oil. This was converted to its hydrochloride salt mp 174°–175° C. (acetone/ether).

$^1$H NMR (HCl salt) (d$^6$DMSO)

δ: 10.55 (br.s, 1H), 8.28 (s,1H), 7.98–8.04 (m,1H), 7.58–7.63 (m,1H), 7.20–7.28 (m,2H), 4.13 (d,2H), 4.08 (d,2H), 3.25–3.40 (m,2H), 2.78–3.13 (m,3H), 2.05–2.23 (m,2H), 1.70–1.95 (m,7H), 1.52–1.70 (m,2H), 1.38–1.50 (m,1H), 0.85 (d,6H).

MS (EI) M$^+$368

Example 21 cis-2,9-H- and trans-2,9-H-Indolizidin-2-ylmethyl-1-methylindole-3-carboxylate (E21a and E21b)

2-Hydroxymethylindolizidine (H. Kato et al, Chem. Pharm. Bull., 1980, 28(7), 2194) (mixture of isomers) was reacted with the acid chloride of 1-methylindole-3-carboxylic acid using the method of Example 1. The isomers were separated by chromatography on silica gel eluting with ethyl acetate. The faster running isomer was crystallised from ether/pentane to fiord the cis isomer (E21a) as a white solid mp 109°–110° C.

$^1$H NMR (CDCl$_3$)

δ: 8.13–8.20 (m,1H), 7.78 (s,1H), 7.25–7.36 (m,3H), 4.21–4.33 (m,2H), 3.82 (s,3H), 3.00–3.08 (m,2H), 2.48–2.60 (m,1H), 2.31 (t,1H), 2.04–2.12 (m,1H), 1.92–2.00 (m,1H), 1.72–1.90 (m,3H), 1.52–1.67 (m,2H), 1.17–1.25 (m,3H).

MS (EI) M$^+$312

The slower running component gave the trans isomer (E21b) as a white solid from ether/pentane mp 94°–96° C.

$^1$H NMR (CDCl$_3$)

δ: 8.10–8.18 (m,1H), 7.78 (s,1H), 7.25–7.38 (m,3H), 4.18–4.31 (m,2H), 3.84 (s,3H), 3.32 (t,1H), 3.05–3.13 (m,1H), 2.65–2.78 (m,1H), 1.50–2.06 (m,9H), 1.17–1.30 (m,2H).

MS (EI) M$^+$312

Example 22 cis-2,9-H- and trans-2,9-H-Indolizidin-2-ylmethyl 1-ethylindole-3-carboxylate (E22a and E22b)

2-Hydroxymethylindolizidine (H. Kato et al, Chem. Pharm. Bull., 1980, 28(7), 2194) (mixture of isomers) was reacted with the acid chloride of 1-ethylindole-3-carboxylic acid using the method of Example 1. The isomers were separated by chromatography on silica gel eluting with ethyl acetate. The faster running component gave the cis isomer (E22a) as a colourless oil and converted to its hydrochloride salt mp 168°–169° C.

$^1$H NMR (HCl salt) (d$^6$DMSO)

δ: 10.90 (br.s, 1H), 8.29 (s,1H), 7.92–8.02 (m,1H), 7.56–7.66 (m,1H), 7.20–7.32 (m,2H), 4.22–4.38 (m,4H), 3.32–3.57 (m,2H), 3.05–3.23 (m,2H), 2.73–2.96 (m,2H), 2.30–2.44 (m,1H), 1.40 (t,3H), 1.25–2.05 (m,7H).

MS (EI) M$^+$326

The slower running component afforded the trans isomer (E22b). Hydrochloride salt mp 146°–148° C.

$^1$H NMR (HCl salt) (d$^6$DMSO)

δ: 10.90 (br.s,1H), 8.20 (s,1H), 7.93–8.03 (m,1H), 7.55–7.65 (m,1H), 7.15–7.33 (m,2H), 4.15–4.40 (m,4H), 3.40–3.75 (m,2H), 2.70–3.30 (m,4H), 1.38 (t,3H), 1.15–2.10 (m,8H).

MS (EI) M$^+$326

Example 23 cis-2,9-H- and trans-2,9-H-Indolizidin-2-ylmethyl-1-n-propylindole-3-carboxylate (E23a and E23b)

2-Hydroxymethylindolizidine CH. Kato et al, Chem. Pharm. Bull., 1980, 28(7), 2194) (mixture of isomers) was reacted with the acid chloride of 1-n-propylindole-3-carboxylic acid using the method of Example 1. The isomers were separated by chromatography on silica gel eluting with ethyl acetate. The faster running component gave the cis isomer (E23a), which was crystallised from pentane mp 54°–55° C. HCl salt mp 172°–173° C. (acetone/ether).

$^1$H NMR (HCl salt) (d$^6$DMSO)

δ: 10.90 (br.s,1H), 8.28 (s,1H), 7.91–8.01 (m,1H), 7.56–7.66 (m,1H), 7.18–7.31 (m,2H), 4.31 (d,2H), 4.24 (t,2H), 3.34–3.54 (m,2H), 3.04–3.24 (m,2H), 2.72–2.94 (m,2H), 2.28–2.43 (m,1H), 1.94–2.06 (m,1H), 1.30–1.90 (m,8H), 0.83 (t,3H).

MS (EI) M$^+$340

The slower running component afforded the trans isomer (E23b), which also crystallised from pentane mp 81°–82° C.

$^1$H NMR (free base) (CDCl$_3$)

δ: 8.10–8.20 (m,1H), 7.83 (s,1H), 7.34–7.42 (m,1H), 7.23–7.33 (m,2H), 4.18–4.32 (m2H), 4.12 (t,2H), 3.28–3.38 (t,1H), 3.04–3.15 (m,1H), 2.64–2.81 (m,1H), 1.47–2.07 (m,11H), 1.13–1.35 (m,2H), 0.95 (t,3H).

MS (EI) M$^+$340

Example 24 cis-4,7-H- and trans-4,7-H-1-Azabicyclo[5.4.0]undecan-4-ylmethylindole-3-carboxylate (E24a and E24b)

The two title compounds (E24a and E24b) were prepared by reaction of indole-3-carboxylic acid chloride with cis-4,7-H-4-hydroxymethyl-1azabicyclo[5.4.0]undecane (D2a) and trans-4,7-H-4-hydroxymethyl-1-azabicyclo[5.4.0]undecane (D2b) respectively, using the method of Example 1. Each product was purified by chromatography on silica gel eluting with chloroform/methanol (19:1) to give a colourless oil. The two isomers had different rf values.

Higher rf isomer: HCl salt mp 130°–135° C.

$^1$H NMR (HCl salt) (CDCl$_3$)

δ: 11.30 (br.s,1H), 10.10 (br.s, 1H), 8.03–8.15 (m,2H), 7.48–7.58 (m,1H), 7.20–7.30 (m,2H), 4.12 (d,2H), 3.30–3.55 (m,2H), 2.50–2.93 (m,3H), 1.60–2.50 (m,12H), 1.30–1.50 (m,1H).

MS (Cl) MH$^+$327

Lower rf isomer: HCl salt mp 160°–162° C. (acetone)

$^1$H NMR (HCl salt) (d$^6$DMSO)

δ: 12.05(s,1H), 10.30(br.s,1H), 8.10(d,1H), 7.94–8.02(m, 1H), 7.45–7.54(m,1H), 7.14–7.25(m,2H), 4.08(d,2H), 2.85–3.60(m,5H), 1.30–2.65(m,13H).

MS (FAB) MH$^+$327

Example 25 cis-5,7-H- and trans-5,7-H-1-Azabicyclo[5.4.0]undecan-5-ylmethylindole-3-carboxylate (E25a and E25b)

Indole-3-carboxylic acid chloride was reacted separately with cis-5,7-H-5-hydroxymethyl-1-azabicyclo[5.4.0]undecane (D3a) and trans-5,7-H-5-hydroxymethyl-1-azabicyclo[5.4.0]undecane (D3b) using the method of Example 1. Each product was purified by chromatography on silica gel eluting with ethyl acetate then ethyl acetate, methanol (95:5). The two isomers had different rf values.

Higher rf isomer: off-white solid mp 109°–110° C.

$^1$H NMR (CDCl$_3$)

δ: 9.05 (br.s,1H), 8.15–8.23 (m,1H), 7.92 (d,1H), 7.35–7.45 (m,1H), 7.20–7.30 (m,2H), 4.15 (d,2H), 2.80–2.90 (m,1H), 2.45–2.72 (m,2H), 2.18–2.42 (m,3H), 1.90–2.05 (m,1H), 1.35–1.87 (m,9H), 1.10–1.35 (m,2H).

MS (CI) MH$^+$327

Lower rf isomer: white solid mp 138°–140° C.

$^1$H NMR(CDCl$_3$)

δ: 9.30 (br.s, 1H), 8.11–8.21 (m,1H), 7.92 (s,1H), 7.38–7.47 (m,1H), 7.22–7.32 (m,2H), 4.07–4.26 (m,2H), 2.83–2.98 (m,2H), 2.05–2.60 (m,5H), 1.15–1.98 (m,11H).

MS (CI) MH$^+$327

Example 26 eq-Quinolizidin-2-ylmethyl-2-methoxyindole-3-carboxylate (E26)

A stirred solution of N-chlorosuccinimide (220 mg, 0.0016 mole) in chloroform (6 ml) at room temperature under nitrogen was treated with a solution of eq-quinolizidin-2-ylmethylindole-3-carboxylate (E9b) (330 mg, 0.0011 mole) in chloroform (6 ml) and stirred for 2 h. The solution was then treated with methanol (0.71 ml, 0.022 mole) and stirring continued. After 3 h a beige precipitate began to form and afar a further 1 h this was filtered off, washed with chloroform,and dried to afford the title compound (E26) as its hydrochloride salt mp 212°–213° C.

$^1$H NMR (HCl salt) (d$^6$DMSO)

δ: 12.10 (s,1H), 10.20 (br.s,1H), 7.80 (d,1H), 7.30 (d, 1H), 7.01–7.17 (m,2H), 4.10 (s,3H), 4.07 (d,2H), 3.23–3.43 (m,2H), 2.73–3.15 (m,3H), 2.00–2.15 (m,1H), 1.35–1.95 (m,10H).

MS (EI) MH$^+$343

Example 27

4-Iodo-3-(eq-quinolizidin-2-yl)methyl-1-isopropylindole carboxylate (E27)

To a solution of eq-quinolizidin-2-ylmethyl-1-isopropylindole-3-carboxylate (E18) (122 mg) in TFA (5 ml), was added thallium trifluoroacetate (170 mg). The reaction mixture was stirred at room temperature for 2 hours then the solvent was removed in vacuo. The residue was treated with Et$_2$O to give a grey solid that was collected by filtration. This was suspended in H$_2$O (5 ml) and a solution of KI (500 mg) in H$_2$O (2 ml) was added. The reaction mixture was stirred at room temperature overnight then extracted thoroughly with CHCl$_3$ (pH 9). The CHCl$_3$ extracts were dried and concentrated in vacuo to give a yellow gum that was purified by column chromatography on SiO$_2$ (CHCl$_3$ 95%, MeOH 5%). The product was isolated as the HCl salt.

$^1$H NMR (250 MHz) (CDCl$_3$) (free base)

δ: 7.79 (s, 1H), 7.8 (dd, 1H), 7.4 (dd, 1H), 6.95 (t,1H), 4.6–4.77 (m,1H), 4.2 (d, 2H), 2.98–3.15 (m,2H), 1.2–2.35 (m,20H inc. d, 6H).

Example 28 eq-Quinolizidin-2-ylmethyl 1-cyclopropylmethylindole-3-carboxylate (E28)

eq-Quinolizidin-2-ylmethyl indole-3-carboxylate (E9b) was alkylated with cyclopropylmethyl bromide using the method in Example 18. The product was chromatographed on silica gel eluting initially with ether, then with ethyl acetate, to afford the title compound (E28) as a colourless oil. This was converted to its hydrochloride salt mp 167°–169° C. (acetone/ether).

$^1$H NMR (HCl salt) (d$^6$DMSO)

δ: 10.55 (br.s, 1H), 8.35 (s, 1H), 7.97–8.05 (m,1H), 7.60–7.70 (m,1H), 7.20–7.30 (m,2H), 4.13 (d,2H and d,2H), 3.22–3.40 (m,2H), 2.74–3.15 (m,3H), 2.02–2.20 (m,1H), 1.25–1.98 (m,11H), 0.40–0.60 (m,4H).

MS (EI) M$^+$366

Example 29 eq-Quinolizidin-2-ylmethyl 1-cyclohexylmethylindole-3-carboxylate (E29)

eq-Quinolizidin-2-ylmethyl indole-3-carboxylate (E9b) was alkylated with cyclohexylmethyl bromide using the method of Example 18. The product was chromatographed on silica gel eluting initially with ether, then with ethyl acetate, to afford a colourless oil, which crystallised from n-pentane to give the title compound (E29) as a white solid mp 98°–100° C.

$^1$H NMR (CDCl$_3$)

δ: 8.13–8.20 (m,1H), 7.79 (s, 1H), 7.20–7.40 (m,3H), 4.18 (d,2H), 3.96 (d,2H), 2.80–2.95 (m,2H), 1.42–2.18 (m,17H), 0.93–1.38 (m,8H).

MS (EI) M$^+$408

Example 30 eq-Quinolizidin-2-ylmethyl 1-acetylindole-3-carboxylate (E30)

eq-Quinolizidin-2-ylmethyl indole-3-carboxylate (E9b) was acylated with acetyl chloride using the method of Example 18. The product was chromatographed on silica gel eluting with ethyl acetate to give a pale yellow oil, which crystallised from ether to afford the title compound (E30) as a white solid mp 127°–129° C.

$^1$H NMR (CDCl$_3$)

δ: 8.42–8.47 (m,1H), 8.10–8.20 (m,2H), 7.35–7.45 (m,2H), 4.23 (d,2H), 2.85–3.00 (m,2H), 2.72 (s,3H), 1.55–2.20 (m,11H), 1.15–1.45 (m,3H).

MS (EI) M$^+$354

Example 31 eq-Quinolizidin-2-ylmethyl 1-acetylmethylindole-3-carboxylate (E31)

A stirred solution of eq-quinolizidin-2-ylmethylindole-3-carboxylate (E9b) (300 mg, 0.96 mmol) in acetone (10 ml) was treated with anhydrous potassium carbonate (270 mg, 2 mmole) and bromoacetone (150 mg, 1.1 mmole) and kept at room temperature for 3 days. The mixture was treated with 10% $Na_2CO_3$ solution (10 ml) and extracted with ethyl acetate (2×25 ml). The combined extracts were dried ($Na_2SO_4$), concentrated in vacuo and the residue chromatographed on silica gel eluting with ethyl acetate/methanol (95:5). The pale yellow oil obtained was crystallised from ether to afford the title compound (E31) as a beige solid (14 mg) mp 139°–142°C.

$^1$H NMR (CDCl$_3$)

δ: 8.17–8.25 (m,1H), 7.81 (s,1H), 7.26–7.35 (m,2H), 7.14–7.22 (m,1H), 4.88 (s,3H), 4.19 (d,2H), 2.82–2.97 (m,2H), 2.14 (s,3H), 1.45–2.20 (m,11H), 1.10–1.40 (m,3H).

MS (EI) M$^+$368

Example 32 cis-2,9-H-N-Methylindolizidin-2-ylmethyl 1-n-propylindole-3-carboxylate iodide (E32)

A stirred solution of cis-2,9-H-indolizidin-2-ylmethyl indole-3-carboxylate (E23), 100 mg, 0.30 mmole) in acetone (10 ml) was treated with iodomethane (0.095 ml, 1.5 mmole) and heated under reflux for 4 h. The solution was then concentrated in vacuo and the residual solid recrystallised from acetone to afford the title compound as a white solid (60 mg, 42%) mp 195°–196° C.

M.S. (Cl) 341

Description 1 (intermediate for Example 2)

3-(2-Hydroxyethyl)quinolizidine (D1)

a) A stirred solution of diisopropylamine (2.25 ml, 0.016 mole) in dry THF (20 ml) at −50° C. under nitrogen was treated with 1.6M n-butyllithium in hexane (9.4 ml, 0.015 mole). After 10 minutes the solution was cooled to −65° C. and treated with a solution of quinolizidin-4-one (I. Murakoshi, Yakugaku Zasshi, 1958, 78, 594) (2.0 g, 0.013 mole) in ether (20 ml), stirred for a further 10 minutes and then ethylene oxide (1.23 g, 0.028 mole) bubbled into the solution, which was allowed to warm to room temperature over 1 hour and then heated under reflux for 1.5 hours. The reaction mixture was treated with concentrated potassium carbonate solution (30 ml) and extracted with ethyl acetate (2×60 ml). The combined extracts were dried ($Na_2SO_4$), concentrated in vacuo and the residue chromatographed on silica gel eluting with chloroform/methanol (98:2) to afford 3-(2-hydroxyethyl)quinolizidin-4-one as a pale yellow oil (1.4 g, 55%).

$^1$H NMR (CDCl$_3$)

δ: 1.16–2.10 (m,12H), 2.30–2.58 (m,2H), 3.18–3.36 (m,1H), 3.62–3.85 (m,2H), 4.20–5.20 (v.br.s, 1H, OH) and 4.70–4.85 (m,1H).

b) A solution of 3-(2-hydroxyethyl)quinolizidin-4-one (1.4 g, 0.0071 mole) in THF (40 ml) was added to a stirred suspension of lithium aluminium hydride (0.5 g, 0.013 mole) in THF (50 ml) under nitrogen and the mixture heated under reflux for 2.5 hours, then cooled to ice bath temperature and treated dropwise with water (0.5 ml), 10% sodium hydroxide solution (0.5 ml) and water (1.5 ml). The mixture was filtered through kieselguhr and the filtrate concentrated in vacuo. The residue was distilled in a Kugelröhr apparatus (bp approx. 140° C. at 2 mmHg) to give the title compound as a colourless oil (0.97 g, 75%).

$^1$H NMR (CDCl$_3$)

δ: 0.88–1.07 and 1.15–2.25 (each m, together 17H), 2.65–2.86 (m,2H), 3.59–3.85 (m,2H).

Description 2 (intermediate for Example 24)

a) Diethylpiperidine-1,2-dipropionate

A stirred solution of ethyl piperidinyl-2-propionate (I Murakoshi, Yakugaku Zasshu, 1958, 78, 598) (0.12 mole) in ethanol (350 ml) was treated with ethyl acrylate (26 ml, 0.24 mole) and heated under reflux for 4 h. The solution was concentrated in vacuo and the residue chromatographed on silica gel eluting with ether to afford the title compound as an yellow oil 9.6 g, (28%).

$^1$H NMR (CDCl$_3$)

δ: 4.14 (q, 4H), 2.93–3.17 (m,1H), 2.70–2.88 (m,2H), 2.46 (t,2H), 2.18–2.40 (m,4H), 1.40–2.00 (m,6H), 1.25 (t,6H), 1.15–1.38 (m,2H).

b) 1-Azabicyclo[5.4.0]undecan-4-one

A solution of diethyl piperidine-1,2-dipropionate (9.60 g, 0.034 mole) in xylene (100 ml) was added dropwise over 4 h to a flask containing 250 ml of xylene, which was being fed via a continuous extraction apparatus to a stirred, refluxing, suspension of sodium hydride (4.2 g of 80%, 0.14 mole) in xylene (100 ml) containing ethanol (0.5 ml) under nitrogen. The reaction mixture was heated under reflux for a total of 40 h, then cooled in an ice bath and treated with 5M HCl acid (250 ml). The aqueous layer was separated, treated with concentrated HCl acid (30 ml) and heated under reflux for 18 h. The solution was cooled, basified with potassium carbonate and extracted with ether (3×100 ml). The combined extracts were dried ($Na_2CO_3$), concentrated in vacuo and the residue distilled in a Kugelröhr apparatus to give the title compound as a colourless oil (4.6 g, 84%) bp approx. 110° C. at 0.25 mm Hg.

$^1$H NMR (CDCl$_3$)

δ: 2.75–3.05 (m,4H), 2.44–2.70 (m,4H), 2.15–2.30 (m,1H), 2.00–2.15 (m,1H), 1.15–1.90 (m,7H).

c) cis-4,7-H- and trans-4–7-H-4-cyano-1-azabicyclo[5.4.0]undecane

A stirred solution of 1-azabicyclo[5.4.0]undecan-4-one (4.60 g, 0.028 mole) and 4-toluenesulphonylmethyl isocyanide (6.73 g, 0.035 mole) in dimethoxyethane (125 ml) together with ethanol (3.2 ml., 0.055 mole) at 5° C. under nitrogen was treated portionwise over 15 minutes with potassium t-butoxide (6.17 g, 0.055 mole) keeping the temperature below 15° C. The mixture was allowed to warm to room temperature over 2 h, then warmed to 45° C. for 0.75 h followed by 18 h at room temperature. The solution was concentrated in vacuo and basified with 10% $Na_2CO_3$ solution, then extracted with ethyl acetate (3×100 ml). The combined extracts were dried ($Na_2SO_4$), concentrated in vacuo and the residue chromatographed on a short neutral alumina column eluting with ethyl acetate to afford a mixture of the title compounds as a pale yellow oil (4.18 g, 84%). This was used without further purification.

¹H NMR (CDCl₃)

δ: 2.60–2.95 (m,4H), 1.15–2.55 (m,14H).

d) Ethyl cis-4,7-H- and trans-4,7-H-1-Azabicyclo[5.4.0]-undecan-4-ylcarboxylate A mixture of cis-4,7-H and trans-4,7-H-4-cyano-1azabicyclo[5.4.0]undecane (D2a and D2b) (3.18 g, 0.018 mole) in concentrated HCl acid (80 ml) was heated under reflux for 12 h, then concentrated in vacuo. The residue was treated with ethanol (80 ml) and concentrated HCl acid (2 ml) and heated under reflux for 6 h, then concentrated in vacuo. The residue was basified with 10% Na₂CO₃ solution (100 ml) and extracted with ethyl acetate (2×100 ml). The combined extracts were dried (Na₂SO₄) and concentrated in vacuo to leave a brown oil, which was chromatographed on silica gel eluting initially with ether, then ethyl acetate, to separate each title compound as a yellow oil.

Higher rf isomer: ¹H NMR (CDCl₃)

δ: 4.10 (q, 2H), 2.62–2.90 (m,2H), 2.35–2.60 (m,2H), 1.25 (t,3H), 1.15–2.30 (m,14H)

Lower rf isomer: ¹H NMR (CDCl₃)

δ: 4.12 (q, 2H), 2.53–2.93 (m,4H), 2.18–2.36 (m,1H), 1.92–2.15 (m,4H), 1.25 (t,3H), 1.15–1.90 (m,9H).

e) cis-4,7-H- and trans-4,7-H-4-Hydroxymethyl-1-azabicyclo[5.4.0]undecane (D2a and D2b).

A stirred suspension of lithium aluminium hydride (232 mg, 0.0061 mole) in THF (20 ml) at room temperature under nitrogen was treated with a solution of one isomer of ethyl 1-azabicyclo[5.4.0]undecan-4-ylcarboxylate (1.10 g, 0.0049 mole) in THF (20 ml). The mixture was stirred for 1 h then treated with water (0.2 ml), 10% NaOH solution (0.2 ml) and water(0.6 ml). The mixture was filtered through a plug of Kieselguhr, the filtrate concentrated in vacuo and the residue distilled in a Kugelröhr apparatus to give one of the title compounds as a colourless oil. The alternative title compound was prepared from the alternative isomer of ethyl 1-azabicyclo[5.4.0]undecan-4-ylcarboxylate using the same procedure, as a colourless oil. The two isomers had different rf values.

Higher rf isomer; ¹H NMR (CDCl₃)

δ: 3.50 (d, 2H), 2.82–2.95 (m,1H), 2.68–2.80 (m,1H), 2.41–2.55 (m,1H), 2.14–2.30 (m,1H), 1.95–2.10 (m,1H), 1.78–1.95 (m,2H), 1.20–1.77 (m,12H)

Lower rf isomer: ¹H NMR (CDCl₃)

δ: 3.45 (d, 2H), 2.65–2.90 (m,2H), 2.48–2.62 (m,1H), 2.20–2.35 (m,1H), 1.15–2.05 (m,15H)

Description 3 (intermediate for Example 25)

a) Ethyl-1-(3-ethoxycarbonylpropyl)piperidin-2-ylacetate

A stirred solution of ethyl piperidin-2-ylacetate (8.0 g, 0.047 mole) and ethyl 4-bromobutyrate (6.7 ml, 0.047 mole) in acetone (100 ml) was treated with potassium carbonate (13 g, 0.094 mole) and heated under reflux for 32 h. A further 1.5 ml of ethyl 4-bromobutyrate and 3 g of potassium carbonate was added and reflux continued for 16 h. The mixture was concentrated in vacuo and the residue treated with water (100 ml) and extracted with ethyl acetate (2×100 ml). The combined extracts were dried (Na₂SO₄), concentrated in vacuo and the residue chromatographed on silica gel eluting with ether/petrol (60–80) to afford the title compound as a pale yellow oil (11.5 g, 86%)

¹H NMR (CDCl₃)

δ: 4.13 (q, 4H), 2.87–3.02 (m,1H), 2.25–2.75 (m,8H), 1.25 (t,6H), 1.15–1.8 (m,8H)

b) 1-Azabicyclo[5,4,0]undecan-5-one

The title compound was prepared from ethyl-1-(3-ethoxycarbonylpropyl)piperidin-2-ylacetate using the method of Description 2b). The crude product was purified by distillation in a Kugelröhr apparatus (bp approx, 105° C. at 0.5 mm Hg) to give a colourless oil.

¹H NMR(CDCl₃)

δ: 2.80–3.20 (m,3H), 1.55–2.65 (m,12H), 1.18–1.50 (m,2H).

c) cis-5,7-H- and trans-5,7-H-5-Cyano-1-azabicyclo[5.4.0]undecane

The title compounds were prepared from 1-azabicyclo [5.4.0]undecan-5-one using the method of Description 2c). The crude product was purified by chromatography on neutral alumina eluting with ethylacetate to afford a yellow oil containing a mixture of the title compounds.

¹H NMR (CDCl₃)

δ: 2.97–3.10 (m), 2.75–2.90 (m), 2.55–2.68 (m), 2.23–2.45 (m), 1.20–2.15 (m).

IR (film) C≡N 2240 cm⁻¹.

d) Ethyl cis-5,7-H- and trans-5,7-H-1-azabicyclo[5.4.0]undecan-5-ylcarboxylate The title compounds were prepared from a mixture of cis-5,7-H-5-cyano-1azabicyclo[5.4.0]undecane and trans-5,7-H-5-cyano-1-azabicyclo[5.4.0]undecane (mixture from Description 3c)) using the method of Description 2d).

The mixture was chromatographed on silica gel eluting initially with ether, then ethylacetate, to afford the separate isomers as yellow oils.

Higher rf isomer: ¹H NMR (CDCl₃) δ: 4.12 (q, 2H), 2.75–2.86 (m,2H), 2.59–2.71 (m,1H), 2.42–2.55 (m,1H), 2.15–2.32 (m,2H), 1.80–2.05 (m,3H), 1.25 (t,3H), 1.15–1.78 (m,9H).

Lower rf isomer: ¹H NMR (CDCl₃)

δ: 4.12 (q, 2H), 2.95–3.10 (m,1H), 2.78–2.90 (m,1H), 2.59–2.73 (m,1H), 2.37–2.49 (m,1H), 2.15–2.28 (m,1H), 1.25 (t,3H), 1.20–2.10 (m,13H).

e) cis-5,7-H- and trans-5,7-H-5-Hydroxymethyl-1-azabicyclo [5.4.0]undecane

The title compounds (D3a and D3b) were prepared respectively from ethyl cis-5,7-H-1-azabicyclo[5.4.0]undecano5-ylcarboxylate and ethylotrans-5,7-H-1-azabicyclo [5.4.0]undecan-5-ylcarboxylate using the method of Description 2e). Each isomer was distilled in a küglelröhr apparatus to give the title compounds as colourless oils.

The isomers had different rf values.

Higher rf isomer: ¹H NMR (CDCl₃)

δ: 3.45–3.60 (m,2H), 2.78–2.92 (m,1H), 2.63–2.74 (m,1H), 2.35–2.56 (m, 3H), 1.92–2.08 (m,1H), 1.20–1.85 (m,13H).

Lower rf isomer:

δ: 3.40–3.60 (m,2H), 2.93–3.10 (m,1H), 2.68–2.90 (2H, m), 2.38–2.52 (m, 1H), 2.15–2.30 (m,1H), 1.15–2.10 (m,14H).

Description 4 (Intermediate for Example 9)

ax-2- Hydroxymethylquinolidine

Ethyl ax-quinolizidin-2ylcarboxylate (E. Koshinaka et al, Yakugaku Zasshi, 1980, 100 (1), 88) was reduced with lithium aluminium hydride using the method of Description 2e). The crude product was distilled in a kugelrohr apparatus (bp approx. 140° C. at 0.2 mm Hg) to afford the title compound (D4) as a colourless oil.

$^1$H NMR (CDCl$_3$)

δ: 3.70 (d, 2H), 2.75–2.86 (m,1H), 2.55–2.66 (m,1H), 1.40–2.24 (m,13H), 1.15–1.37 (m,2H).

Description 5 (Intermediate for Example 10)

eq-2-(2-Hydroxyethyl)quinolizidine

Ethyl-eq-quinolizidin-2-ylacetate (U.S. Pat. No. 3,692, 791) was reduced with lithium aluminium hydride using the method of Description 2e). The product was purified by distillation in a Kugelrohr apparatus (bp approx. 120° C. at 0.15 mm Hg) to afford the title compound (D5) as a colourless oil.

$^1$H NMR (CDCl$_3$)

δ: 3.63–3.75 (m,2H), 2.84 (dt,2H), 1.90–2.13 (m,2H), 1.15–1.80 (m,14H), 0.90–1.10 (m,1H).

Description 6 (intermediate for Example 14)

cis-1,9-H-and trans-1,9-H-1-Hydroxymethylindolizidine (D6a and D6b)

The title compounds (D6a and D6b) were prepared respectively from ethyl cis-1,9-H- and trans-1,9-H-indolizidin-1-carboxylates (H. Kato et al, Chem Pharm Bull., 1980, 28, 2194) using the method of Description 2e). Each isomer was obtained as a colourless oil.

cis isomer: $^1$H NMR (CDCl$_3$)

δ: 4.50 (br.s, 1H), 3.86 (dd, 1H), 3.46 (dd, 1H), 3.03–3.18 (m,2H), 1.38–2.17 (m,11H), 1.15–1.32 (m,1H).

trans isomer: $^1$H NMR (CDCl$_3$)

δ: 3.57–3.72 (m,2H), 2.97–3.13 (m,2H), 1.74–2.20 (m,7H), 1.40–1.70 (m, 4H), 1.12–1.35 (m,2H).

5-HT$_4$ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% CO$_2$ in O$_2$ and maintained at 37° C. In all experiments, the Krebs solution also contains methiothepin 10–7M and granisetron 10–6M to block effects at 5-HT$_1$, 5-HT$_2$ and 5-HT$_3$ receptors.

After construction of a simple concentration-response curve with 5-HT,min using 30s contact times and a 15 min dosing cycle, a concentration of 5-HT is selected so as to obtain a contraction of the muscle approximately 40–70% maximum (10$^9$M approx). The tissue is then alternately dosed every 15 min with this concentration of 5-HT and then with an approximately equi-effective concentration of the nicotine receptor stimulant, dimethylphenylpiperazinitun (DMPP). After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, pIC$_{50}$ values are determined, being defined as the –log concentration of antagonist which reduces the contraction by 50%. A compound which reduces the response to 5-HT but not to DMPP is believed to act as a 5-HT$_4$ receptor antagonist.

Compounds were generally active in the range of concentrations of the order of pIC$_{50}$=6 or more, E22a and E26 showing particularly good activity.

2) Piglet Atria

Compounds were tested in the piglet spontaneous beating screen (Naunyn-Schmiedeberg's Arch. Pharmacol 342, 619–622). pK$_B$ (–log10 K$_B$) value for the compounds were generally 6 or more, E5a, E9b, E16, E18, E21a, E22a, E24a, E24b, E26, E27 and E30 showing particularly good activity.

3) Rat oesophagus

Rat oesophageal tunica muscularis mucosae is set up according to Baxter et. al. Naunyn-Schmiedeberg's Arch. Pharmacol., 343,439–446 (1991). The inner smooth muscle tube of the muscularis mucosae is isolated and mounted for isometric tension recording in oxygenated (95% O$_2$/5% CO$_2$) Tyrodes solution at 37° C. All experiments are performed in pargyline pretreated preparations (100 μM for 15 min followed by washout) and in the presence of cocaine (30 μM). Relaxant responses to 5-HT are obtained after pre-contracting the oesophagus tissue with carbachol (3μM).

4) 5-HT-induced motility in dog gastric pouch

Compounds are tested for inhibition in the in vivo method described in "Stimulation of canine motility by BRL 24924, a new gastric prokinetic agent", Bermudez et al, J. Gastrointestinal Motility, 1990, 2(4), 281–286.

We claim:

1. A compound of formula (I), or a pharmaceutically acceptable salt thereof

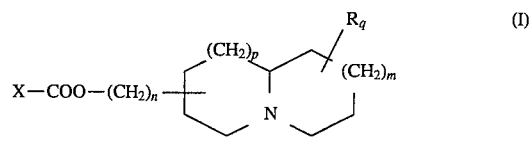

wherein X is of subformula (a) or (b):

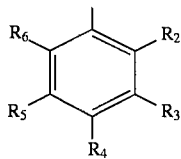
(b)

wherein

L is N or CR$_c$ wherein R$_c$ is hydrogen, C$_{1-6}$alkoxy, halo, C$_{1-6}$alkyl or cyano;

Q is NR$_1$;

R$_a$ is hydrogen, halo, C$_{1-6}$alkyl, amino, nitro or C$_{1-6}$alkoxy;

R$_b$ is hydrogen, halo, C$_{1-6}$alkyl or C$_{1-6}$alkoxy;

R$_1$ is hydrogen, C$_{1-10}$alkyl, C$_{2-6}$alkenyl, aralkyl, C$_{2-6}$alkanoyl, or C$_{2-6}$alkanoyl C$_{1-3}$alkyl;

R$_2$ is methoxy; and

R$_3$ is hydrogen, chloro or fluoro;

R$_4$ is amino optionally substituted by a C$_{1-6}$alkyl group;

R$_5$ is halo;

R$_6$ is hydrogen, halo, C$_{1-6}$alkoxy or amino;

n is 0, 1, 2, 3, or 4;

p and m are independently 0, 1 or 2; and

R$_q$ is hydrogen or C$_{1-6}$alkyl.

2. A compound according to claim 1 wherein X is of sub-formula (a) and L is CH, C—CH$_3$, C—Cl or COCH$_3$.

3. A compound according to claim 1 wherein X is of sub-formula (a) and Q is NR$_1$ wherein R$_1$ is hydrogen or a methyl or ethyl group.

4. A compound according to claim 1 wherein X is of sub-formula (a) and R$_a$ is hydrogen and R$_b$ is hydrogen or iodo.

5. A compound according to claim 1 wherein X is of sub-formula (b) and R$_2$ is methoxy, R$_4$ is amino and R$_5$ is halo.

6. A compound according to claim 1 wherein p=m=1; p=0, m=1; p=1 or m=2; p=2, m=1.

7. A compound according to claim 1 wherein R$_q$ is hydrogen.

8. A compound according to claim 1 wherein the X—COO—(CH$_2$)$_n$— is attached such that the number of carbon atoms between the ester linkage and the azabicydic nitrogen atom is from 2 to 4 carbon atoms.

9. A pharmaceutical composition comprising a compound according to claim 1, and a pharmaceutically acceptable carrier.

10. A compound according to claim 2 wherein Q is NR$_1$ wherein R$_1$ is hydrogen or a methyl or ethyl group.

11. A compound according claim 10 wherein R$_a$ is hydrogen and R$_b$ is hydrogen or iodo.

12. A compound according to claim 11 wherein p=m=1; p=0, m=1; p=1 or m=2; p=2, m=1.

13. A compound according to claim 12 wherein R$_q$ is hydrogen.

14. A compound according to claim 1 wherein X is of sub-formula (b) and R$_2$ is methoxy, R$_4$ is amino and R$_5$ is halo.

15. A compound selected from the group consisting of: 3-ax- and 3-eq-quinolizidin-3-ylmethylindole-3-carboxylate, 3-ax- and 3-eq-quinolizidin-3-ylethylindole-3-carboxylate, 3-ax- and 3-eq-quinolizidin-3-ylindole-3-carboxylate, 2-ax- and 2-eq-quinolizidin-2-ylindole-3-carboxylate, cis-2,9-H- and trans-2,9-H-indolizidin-2-ylmethylindole-3-carboxylate, cis-2,9-H- and trans-2,9-H-indolizidin-2-ylethylindole-3-carboxylate, 3-ax- and 3-eq-quinolizidin-3-ylmethyl-1-methylindazole-3-carboxylate, 3-ax- and 3-eq-quinolizidin-3-ylmethyl-4-amino-5-chloro-2-methoxybenzoate, ax- and eq-quinolizidin-2-ylmethylindole-3-carboxylate, eq-quinolizidin-2-ylethylindole-3-carboxylate, eq- and ax-quinolizidin-1-ylindole-3-carboxylate, ax-and eq-quinolizidin-1-ylmethylindole-3-carboxylate, cis-1,9-H- and trans-1,9-H-indolizidin-1-ylindole-3-carboxylate, cis- and trans-1,9-H-indolizidin-1-ylmethylindole-3-carboxylate, eq-quinolizidin-2-ylmethyl-1-methylindole-3-carboxylate, eq-quinolizidin-2-ylmethyl-1-ethylindole-3-carboxylate, eq-quinolizidin-2- ylmethyl-1-n-propylindole-3-carboxylate, eq-quinolizidin-2-ylmethyl-1-isopropylindole-3-carboxylate, eq-quinolizidin-2-ylmethyl-1-allylindole-3-carboxylate, eq-quinolizidin-2-ylmethyl-1-isobutylindole-3-carboxylate, cis-2,9-H- and trans-2,9-H-indolizidin-2-ylmethyl-1-methylindole-3-carboxylate, cis-2,9-H- and trans-2,9-H-indolizidin-2-ylmethyl-1-ethylindole-3-carboxylate, cis-2,9-H- and trans-2,9-H-indolizidin-2-ylmethyl-1-n-propylindole-3-carboxylate, cis-4,7-H- and trans-4,7-H-1-azabicyclo[5.4.0]undecan-4-ylmethylindole-3-carboxylate, cis-5,7-H- and trans-5,7-H-1-azabicyclo[5.4.0] undecan-5-ylmethylindole-3-carboxylate, eq-quinolizidin-2-ylmethyl-2-methoxyindole-3-carboxylate, 4-iodo-3-(eq-quinolizidin-2-yl)methyl-1-isopropylindole carboxylate, eq-quinolizidin-2-ylmethyl 1-cyclopropylmethylindole-3-carboxylate, eq-quinolizidin-2-ylmethyl 1-cyclohexylmethylindole-3-carboxylate, eq-quinolizidin-2-ylmethyl 1-acetylindole-3-carboxylate, eq-quinolizidin-2-ylmethyl 1-acetylmethylindole-3-carboxylate, cis-2,9-H-N-methylindolizidin-2-ylmethyl 1-n-propylindole-3-carboxylate iodide, including pharmaceutically acceptable salts thereof.

* * * * *